United States Patent [19]

Sawamura et al.

[11] Patent Number: 5,133,774
[45] Date of Patent: Jul. 28, 1992

[54] TEACHING PLAYBACK SWING-PHASE-CONTROLLED ABOVE-KNEE PROSTHESIS

[75] Inventors: Seishi Sawamura, Kobe; Sakuya Nakajima, Nishinomiya; Kunio Amemori, Kobe; Hidehisa Oku, Akashi; Akio Nakagawa, Itami; Ichiro Kitayama, Kobe; Hiromu Matsuda, Akashi; Katsuhiko Yoshida, Takasago; Masaru Takeda, Kobe; Toshio Nakane, Akashi; Shiro Horiguchi, Hyogo; Shigeru Yuki, Nishinomiya, all of Japan

[73] Assignee: Kabushiki Kaisha Kobe Seiko Sho, Kobe, Japan

[21] Appl. No.: 709,290

[22] Filed: Jun. 3, 1991

Related U.S. Application Data

[62] Division of Ser. No. 327,894, Mar. 23, 1989, Pat. No. 5,062,856.

[30] Foreign Application Priority Data

| Mar. 25, 1988 | [JP] | Japan | 63-72943 |
| Mar. 25, 1988 | [JP] | Japan | 63-72944 |
| Mar. 25, 1988 | [JP] | Japan | 63-72945 |

[51] Int. Cl.$^5$ .......................... A61F 2/64; A61F 2/70; A61F 2/74
[52] U.S. Cl. ........................ 623/24; 623/26; 623/43; 623/44; 623/27
[58] Field of Search .............. 623/24, 25, 43, 44, 623/26–42, 45, 46

[56] References Cited

U.S. PATENT DOCUMENTS 4,876,944  10/1989  Wilson et al. ............. 623/24 X

FOREIGN PATENT DOCUMENTS

| 3028608 | 2/1982 | Fed. Rep. of Germany . |
| 2740804 | 7/1984 | Fed. Rep. of Germany . |
| 2623086 | 5/1989 | France .................. 623/25 |
| 51-247638 | 12/1977 | Japan . |
| 1447366 | 12/1988 | U.S.S.R. ................ 623/39 |
| 2149004 | 6/1985 | United Kingdom . |
| 2201260 | 8/1988 | United Kingdom ........ 623/25 |

OTHER PUBLICATIONS

Nakagawa et al., "All-In-One-Intelligent Above Knee Prosthesis", Bio-Mechanism 8, Sep. 1986: Tokyo University, pp. 227≧235.
Rosen et al., "Modification of Spastic Gait Through Mechanical Dumping", IFAC Control Aspects of Prosthetics and Orthetics, May 1982.

*Primary Examiner*—Randall L. Green
*Assistant Examiner*—D. Willse
*Attorney, Agent, or Firm*—Oblon, Spivak, McClelland, Maier & Neustadt

[57] ABSTRACT

A teaching playback swing-phase-controlled above-knee prosthesis comprises a thigh frame, a leg frame an air cylinder interconnecting the thigh and leg frames and provided with adjusting means for adjusting the degree of opening the valve of the air cylinder to a plurality of degrees respectively for a plurality of walking speeds selected during trial walking, a gait selecting switch having positions respectively for setting degrees of opening of the valve of the air cylinder in a teaching mode and for playback mode in which one of the degrees of opening is selected according to an actual walking speed, an opening detector for detecting the degree of opening of the valve of the air cylinder, an opening storage device for storing a plurality of set degrees of opening of the valve of the air cylinder, a phase detector for detecting swing phases and stance phases, walking speed detector for detecting an acutal walking speed, and control unit for adjusting the degree of opening of the valve of the air cylinder in one of the set degrees of opening corresponding to the actual walking speed. The teaching playback swing-phase-controlled above-knee prosthesis is capable of automatically controlling the speed of swing motion of the leg frame according to the actual walking speed of the prosthesis wearer.

5 Claims, 7 Drawing Sheets

TEACHING PLAYBACK SWING-PHASE-CONTROLLED ABOVE-KNEE PROSTHESIS

This is a division of application Ser. No. 07/327,894, filed on Mar. 23, 1989, now U.S. Pat. No. 5,062,856.

BACKGROUND OF THE INVENTION

1. Field of the Invention

The present invention relates to a method of operating an above-knee prosthesis and, more particularly to a pneumatically or hydraulically controlled teaching playback swing-phase-controlled above-knee prosthesis.

2. Description of the Prior Art

The artificial leg is designed so that a person wearing the artificial leg cannot be easily identified thus avoiding exerting mental and physical stresses on the person.

Figure 15:
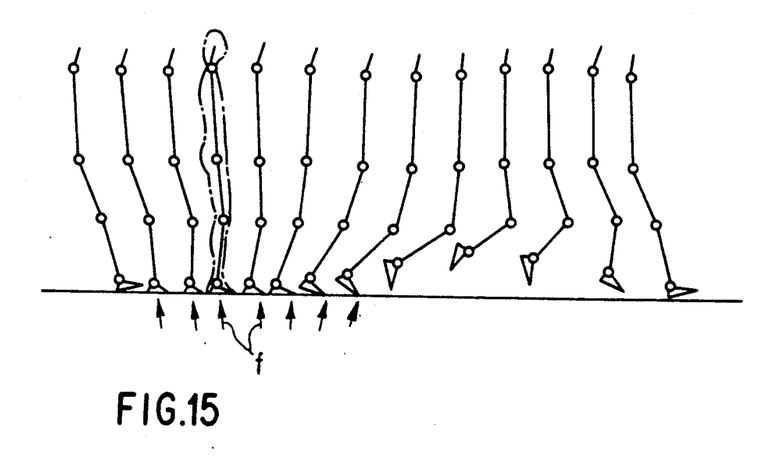
FIG. 15 is a diagrammatic illustration showing the sequential variations of the posture of a normal person during walking.

FIG. 15 is a diagrammatic illustration showing the sequential variation of the posture of the right half of a normal person, in which indicated at a is the heel, at b is the knee, at c is the hip, at d is the leg, at e is the thigh. In a stance phase between the landing of the heel a on the floor and the departure of the toe g from the floor, a substantially vertical reaction f of the floor acts on the leg d. A phase between the departure of the toe g from the floor and the next landing of the heel a on the floor is a swing phase.

Figure 16:
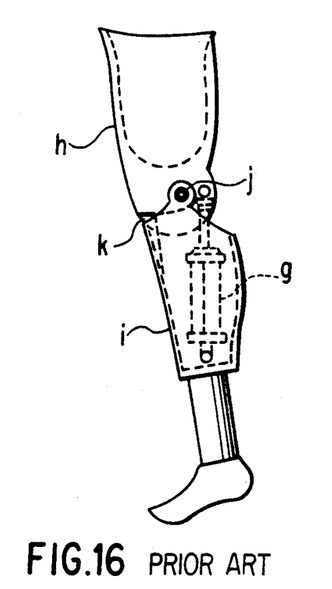
FIG. 16 is a side elevation of a conventional above-knee prosthesis.

FIG. 16 shows a conventional above-knee prosthesis incorporating an air cylinder g, disclosed in Japanese Patent Publication No. 52-47638. A thigh frame h and a leg frame i are joined pivotally by a knee shaft j, the extremity of the piston rod of the air cylinder g is joined pivotally to the thigh frame h, and the lower end of the cylinder of the air cylinder g is joined pivotally to the leg frame i. Since the leg frame i swings as a pendulum in a swing phase, a resistance against the flow of air and the expansionary force of compressed air in the air cylinder g serve in substitution for muscles. Thus, the air cylinder g suppresses the upward swing of the heel in the initial stage of a swing phase, allows the subsequent free forward swing of the leg frame i, and brakes the forward swing of the leg frame i in the final stage of the swing phase to mitigate terminal impact. In a stance phase subsequent to the swing phase, the thigh frame h and the leg frame i come into abutment with a stopper k, whereby the knee joint is prevented from drop-off.

Figure 17A:
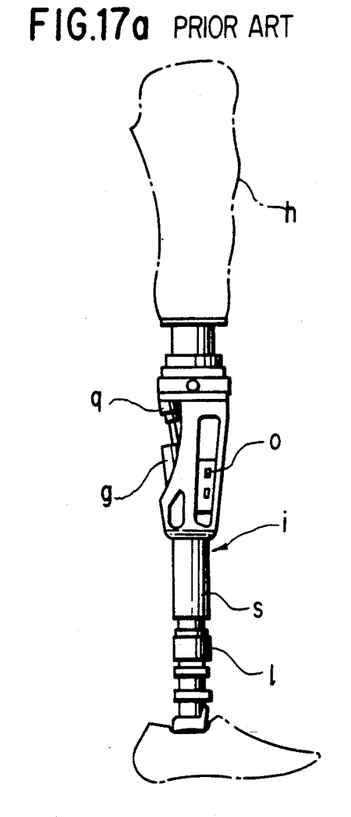
FIG. 17(a) is a side elevation of another conventional above-knee prosthesis.
Figure 17B:
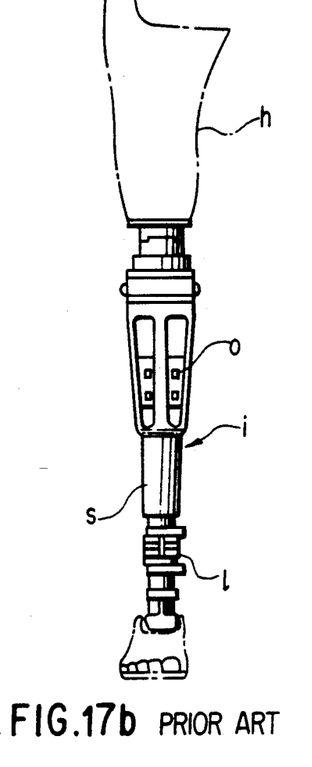
FIG. 17(b) is a front elevation of the above-knee prosthesis of FIG. 17(a)
Figure 17C:
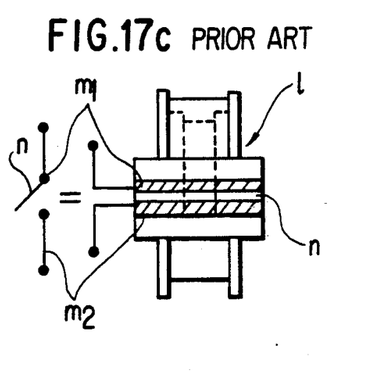
FIG. 17(c) is a schematic illustration of a pressure switch incorporated into the above-knee prosthesis of FIG. 17(a)
Figure 17D:
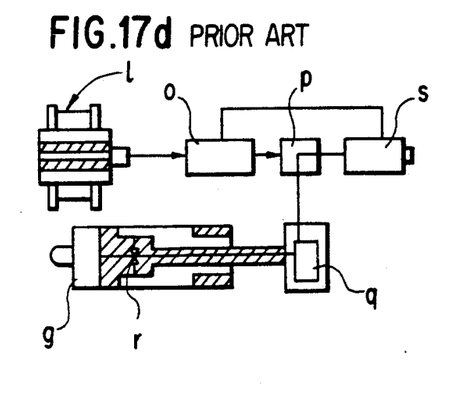
FIG. 17(d) is a block diagram of a control system for controlling the above-knee prosthesis of FIG. 17(a).

FIGS. 17(a), 17(b), 17(c) and 17(d) show another conventional above-knee prosthesis. As shown in FIG. 17(c), a pressure switch consisting of metallic plates m1 and m2 and a compression-conductive rubber plate n placed between the metallic plates m1 and m2 is closed when a pressure exceeding a predetermined level is applied thereto. Then, a microcomputer o (FIG. 17(d)) gives a signal to a driver p to drive a rotary solenoid q so as to control the opening of the valve r of an air cylinder g. In FIGS. 17(a) to 17(d), indicated at s is a power supply.

The motion of the leg frame i relative to the thigh frame h in a swing phase is controlled in a plurality of walking speeds according to a control program organized on the basis of simulated results from dynamic analysis of various gaits of the normal persons. Therefore, the motion of the leg frame i can be controlled so as to meet different gaits of the normal persons, namely, a gait for normal walking, a gait for rambling and a gait for quick walking, and this above-knee prosthesis is comparatively satisfactory in motion. However, this above-knee prosthesis has the following structural drawbacks to be improved.

(1) The pressure switch requires a large space for installation, which increases the total length of the above-knee prosthesis. Therefore, it is difficult to use the above-knee prosthesis for children and women.

(2) It is highly possible that the pressure switch malfunctions due to variations in the reaction of the ground resulting from variations in the condition of the ground or due to the abrasion of the shafts and sliding parts, which may change to cause problems in the safety of a person wearing the above-knee prosthesis (hereinafter, referred to as "prosthesis wearer").

(3) The pressure switch is a kind of contact sensor having contact parts which are abraded to reduce the life of the pressure switch.

(4) The above-knee prosthesis requires comparatively troublesome work for adjustment and maintenance.

(5) The exposed wiring of the pressure switch is subject to breakage.

(6) The displacement of the movable parts of the above-knee prosthesis relative to each other for closing and opening the pressure switch is a possible cause of malfunction of the pressure switch and deteriorates walking feeling.

(7) Since the pressure switch and associated parts are provided at a lower position on the leg frame, the sensed weight of the above-knee prosthesis is greater than the actual weight of the same.

SUMMARY OF THE INVENTION

Accordingly, it is an object of the present invention to provide an above-knee prosthesis capable of maintaining a resistance against drop-off for a sufficient time period in a stance phase without depending on the weight of the prosthesis wearer.

It is another object of the present invention to provide a swing-phase-controlled above-knee prosthesis capable of automatically control of the motion of the above-knee prosthesis according to the intention of the prosthesis wearer among a plurality of set walking speeds previously determined specially for the prosthesis wearer and capable of optionally changing the set walking speeds through a simple operation.

It is a further object of the present invention to provide a swing-phase-controlled above-knee prosthesis capable of discriminating between a stance phase and a swing phase by detecting the angle between a thigh frame and a leg frame by an angle detector, instead of detecting a stance phase by means of a pressure switch which is closed when a load exceeding a predetermined level is applied thereto.

In a first aspect of the present invention, a teaching playback swing-phase-controlled above-knee prosthesis comprises a thigh frame, a leg frame pivotally joined to the thigh unit with a knee joint pin, an air cylinder interconnecting the thigh and leg units and provided with an opening adjusting screw for adjusting the opening of the valve of the air cylinder to a plurality of values for a plurality of walking speeds selected during trial walking, gait selecting means having a plurality of positions including those which may be selected in a teaching mode for setting degrees of opening of the valve of the air cylinder respectively for the plurality of walking speeds and that to be selected for a playback mode, opening detecting means for detecting the degree of opening of the valve of the air cylinder, opening storage means for storing a plurality of degrees of opening of the valve of the air cylinder set respectively for the plurality of walking speeds, phase detecting means for detecting swing during walking and stance phases, walking speed determining means for determining an actual walking speed on the basis of the lengths of swing phases and stance phases detected by the phase detecting means, and control means for adjusting the degree of opening of the valve of the air cylinder to one of the values of opening corresponding to the actual walking speed detected by the walking speed detecting means.

In a second aspect of the present invention, the teaching playback swing-phase-controlled above-knee prosthesis in the first aspect of the present invention comprises an angular variation detecting means for detecting the variation of the angle between the thigh frame and the leg frame.

In a third aspect of the present invention, the teaching playback swing-phase-controlled above-knee prosthesis in the first or second aspect of the present invention further comprises a braking device for braking the drop-off motion of the leg frame, comprising brake disk, a movable brake shoe, and a return spring biasing the brake shoe away from the brake disk; a pneumatic actuator having a hermetic chamber and operatively connected to the brake shoe; an air passage connecting the upper chamber of the air cylinder to the hermetic chamber of the pneumatic actuator and provided with a check valve; an air passage connecting the hermetic chamber of the pneumatic actuator to the lower chamber of the air cylinder and provided with a check valve and a metering valve; and an air passage connecting the lower chamber of the air cylinder to the upper chamber of the same and provided with a check valve and a metering valve.

According to the present invention, in training a prosthesis wearer wearing an above-knee prosthesis of the present invention, average stance phase durations and openings of the valve of the air cylinder respectively for different walking speeds are stored in a memory. When the prosthesis wearer walks at an optional walking speed, an actual stance phase duration is detected by phase detecting means or the angular variation detecting means, and then an opening corresponding to the actual stance phase duration is selected so that the motion of the above-knee prosthesis is controlled according to the walking speed of the prosthesis wearer.

According to the present invention, the piston of the air cylinder reaches the uppermost position in the cylinder body of the air cylinder in a stance phase to discharge air from the upper chamber of the air cylinder into the actuator means, and thereby the actuator means diminishes in length to apply the knee brake unit by pulling the movable brake shoe, so that the knee joint is braked for a predetermined time to prevent drop-off. The air supplied into the actuator means is discharged gradually into the lower chamber of the air cylinder through the metering valve and the check valve, so that the braking force decreases gradually to zero in a predetermined time.

BRIEF DESCRIPTION OF THE DRAWINGS

The above and other objects, features and advantages of the present invention will become more apparent from the following description taken in conjunction with the accompanying drawings, in which.

DESCRIPTION OF THE PREFERRED EMBODIMENTS

Figure 1:
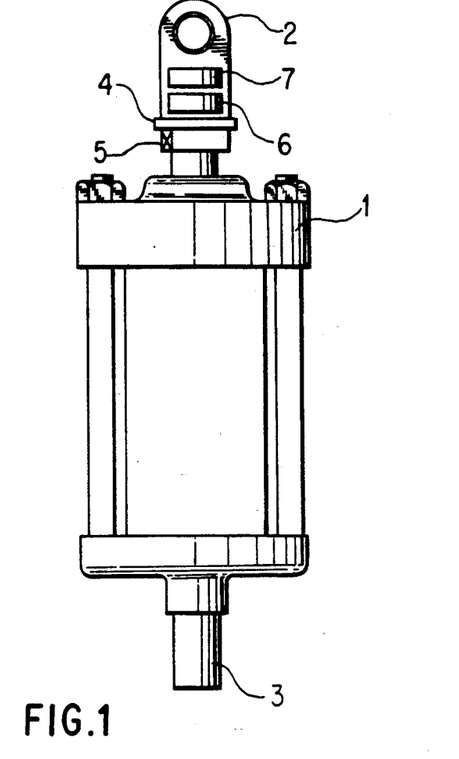
FIG. 1 is a side elevation of an air cylinder incorporated into a teaching playback swing-phase-controlled above-knee prosthesis (hereinafter, referred to simply as "above-knee prosthesis") in a first embodiment according to the present invention.
Figure 2:
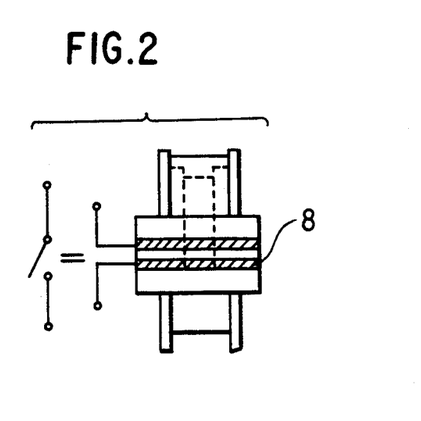
FIG. 2 is a schematic side elevation of a pressure switch employed in the above-knee prosthesis of FIG. 1.
Figure 3:
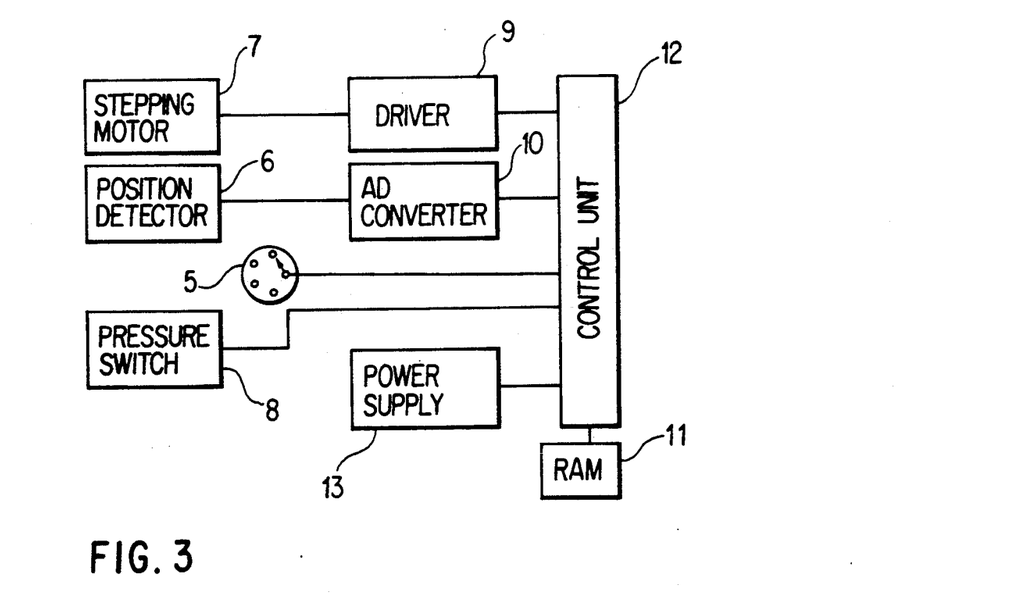
FIG. 3 is a block diagram of a control system incorporated into the above-knee prosthesis of FIG. 1.

First Embodiment (FIGS. 1 to 3):

Referring to FIGS. 1 and 2, an above-knee prosthesis in a first embodiment according to the present invention comprises a thigh frame, not shown, a leg frame, not shown, an air cylinder 1 having a piston with an upper joining end 2 pivotally joined to a thigh frame, and a lower joining end 3 pivotally joined to a leg frame. an externally adjustable adjusting screw 4 provided on the upper joining end 2, a screw rod, not shown, engaging the adjusting screw 4, and a control system. The air cylinder 1 is mounted on the leg frame at a lower joining. The opening of the air valve of the air cylinder 1 is adjusted by the adjusting screw to adjust the speed of the motion of the above-knee prosthesis.

The control system comprises a speed setting gait selective means 5 having a plurality of setting positions, namely, a playback position, a low-speed position, a middle-speed position and a high-speed position, and provided under the adjusting screw 4, a position detector 6 disposed above the adjusting screw 4 to detect the opening of the valve of the air cylinder 1 through the detection of the position of the adjusting screw 4, a stepping motor 7 disposed above the position detector 6, a pressure switch 8 (FIG. 3) provided on the leg frame to detect load on the leg frame, a driver 9 for driving the stepping motor 7, and AD converter 10 for converting the analog detection signal of the position detector 6 into a corresponding digital signal, a RAM (Random access memory) 11 for storing data obtained by the position detector 6 and the pressure switch 8, a control unit 12, and a power supply 13. The stepping motor 7 adjusts the opening of the valve of the air cylinder 1 according to instructions of a controller 12. The pressure switch 8 is provided on the leg frame. The driver 9, the AD converter 10, the RAM 11, the control unit 12 and the power supply 13 of the control system are integrated with a microcomputer and are contained in the cylinder body of the air cylinder 1.

In teaching operating conditions of the above-knee prosthesis suitable for a prosthesis wearer, the speed setting switch 5 is set at the low-speed position. Then, the opening of the valve of the air cylinder 1 is adjusted to an appropriate value $S_{SLOW}$ for low-speed walking by operating the adjusting screw 4. The opening $S_{SLOW}$ for low-speed walking is detected by the position detector 6 and is stored in the RAM 11. Then, the prosthesis wearer starts walking at a low walking speed. While the prosthesis wearer is walking, a stance phase period, namely, a time period in which the pressure switch 8 is closed, is measured and the total of the stance phase periods is divided by the number of the walking steps to determine an average low-speed stance phase period $T_{SLOW}$. The average low-speed stance phase period $T_{SLOW}$ is stored in the RAM 11.

Then, the speed setting switch 5 is set at the middle speed position, the opening of the valve of the air cylinder 1 is adjusted to an appropriate value $S_{MID}$ for middle-speed walking, and then the prosthesis wearer walks at a middle walking speed. While the prosthesis wearer is walking at the middle walking speed, an average middle-speed stance phase period $T_{MID}$ is determined in the same manner. The opening $S_{MID}$ for middle-speed walking and the average middle-speed stance phase period $T_{MID}$ are stored in the RAM 11.

Similarly, an opening $S_{FAST}$ and an average high-speed stance phase period $T_{FAST}$ for high-speed walking are determined and stored in the RAM 11.

Then, the speed setting switch 5 is set at the playback position, the opening of the valve of the air cylinder 1 is set at the opening $S_{SLOW}$, and then the prosthesis wearer starts walking at an arbitrary walking speed. While the prosthesis wearer is walking, closed periods of the pressure switch 8 representing stance phase periods T are stored sequentially in the RAM 11. The control unit 12 compares the stance phase periods T sequentially with the average low-speed stance phase period $T_{SLOW}$, the average middle-speed stance phase period $T_{MID}$ and the average high-speed stance phase period $T_{FAST}$, and gives an instruction to the driver 9 to adjust the opening of the valve of the air cylinder 1 to an opening $S_T$ appropriate to the stance phase period T by the stepping motor 7. The appropriate opening $S_T$ is decided in the following manner.

1) When $T \geq (T_{SLOW}+T_{MID})/2$, $S_T$ is adjusted to $S_{SLOW}$.
2) When $(T_{MID}+T_{FAST})/2 \leq T \leq (T_{SLOW}+T_{MID})/2$, $S_T$ is adjusted to $S_{MID}$.
3) When $T<(T_{MID}+T_{FAST})/2$, $S_T$ is adjusted to $S_{FAST}$.

If the feeling of gaits at walking speeds respectively corresponding to the openings $S_{SLOW}$, $S_{MID}$ and $S_{FAST}$ is different from that of gaits at walking speeds respectively corresponding to the initial set openings, the openings are readjusted properly.

Thus, factors affecting the motion of the above-knee prosthesis are set on the basis of prosthesis wearer's gaits, i.e., on the basis of a walking speed normal for that wearer instead of the simulated results from a large quantity of data of normal person's gaits as in conventional above knee prothesis. Accordingly, the prosthesis wearer is able to walk with gaits precisely suiting prosthesis wearer's physical characteristics. Furthermore, since the mode of motion of the above-knee prosthesis is controlled automatically according to the actual prosthesis wearer's gait, the prosthesis wearer is able to walk with a gait suited to prosthesis wearer's physical condition. Still further, the setting of the above-knee prosthesis can be adjusted by the prosthesis wearer without troubling other persons.

Figure 4:
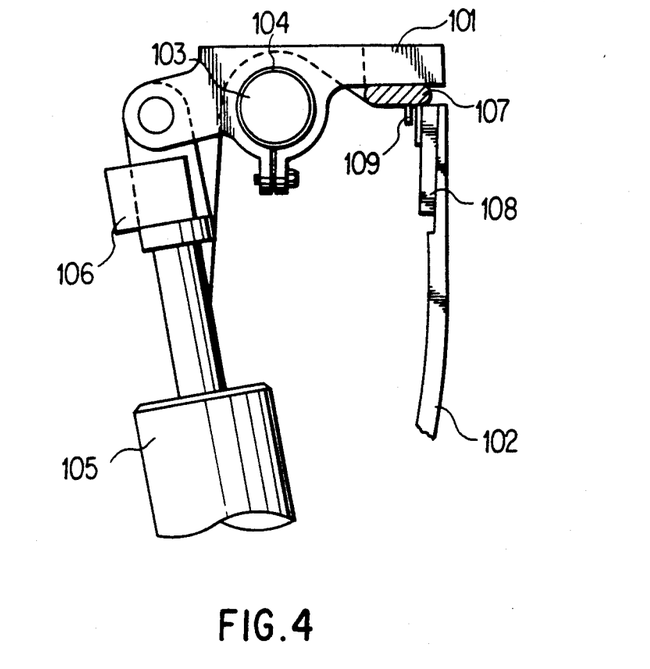
FIG. 4 is a fragmentary longitudinal sectional view showing an essential portion of an above-knee prosthesis in a second embodiment according to the present invention.
Figure 5:
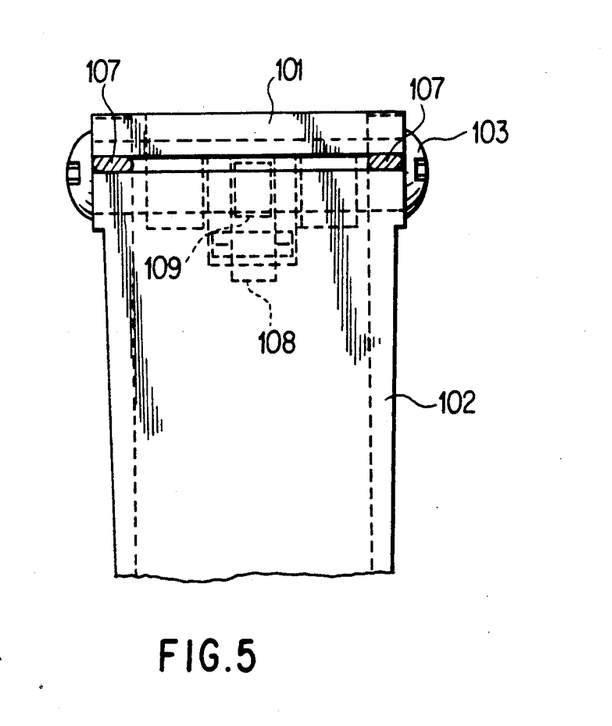
FIG. 5 is a front elevation corresponding to FIG. 4.

Second Embodiment (FIGS. 4 to 8):

Referring to FIGS. 4 and 5, a thigh frame 101 and a leg frame 102 are joined pivotally by a knee joint pin 103. In this embodiment, the knee joint pin 103 is fixed to the leg frame 102 and is rotatably fitted in a bush 104 fixed to the thigh frame 101 so that the thigh frame 101 is able to turn on the knee joint pin 103 relative to the leg frame 102.

The extremity of the piston rod of an air cylinder 105 is joined pivotally to a rear extension of the thigh frame 101, and the lower end of the cylinder body, not shown, of the air cylinder 105 is joined pivotally to the leg frame 102. The air cylinder 105 is provided with a valve, not shown, for controlling the flow of air, and a rotary solenoid 106 for driving the valve. Rubber pads 107 are provided respectively on the opposite sides of the upper end of the leg frame 102 so as to be compressed between a front extension formed at the lower end of the thigh frame 101 and the upper end of the leg frame when the leg frame 102 swings forward relative to the thigh frame 101 to stop the swing motion of the leg frame 102 beyond a limit. A knee angle detector 108 (a proximity detector) is provided in front of the knee joint pin 103 and is attached to the inner surface of the front portion of the upper end of the leg frame 102, and a metallic plate 109 is attached to the front extension of the thigh frame 101 so as to correspond to the knee angle detector 108. The knee angle detector 108 detects an angle between the thigh frame 101 and the leg frame 102 from the position of the metallic plate 109 relative to the knee angle detector 108. A control unit decides whether the above-knee prosthesis is in a stance phase or in a swing phase from the variation of detection signals representing the variation of the knee angle given thereto from the knee angle detector 108. Then, the control unit provides control signals for controlling the opening of the valve of the air cylinder 105 in multiple steps by the rotary solenoid 106 so that the swing motion of the leg frame 102 is controlled properly for a swing phase in a manner similar to that in the first embodiment except that the walking speed is determined by the phase detector.

Figure 6:
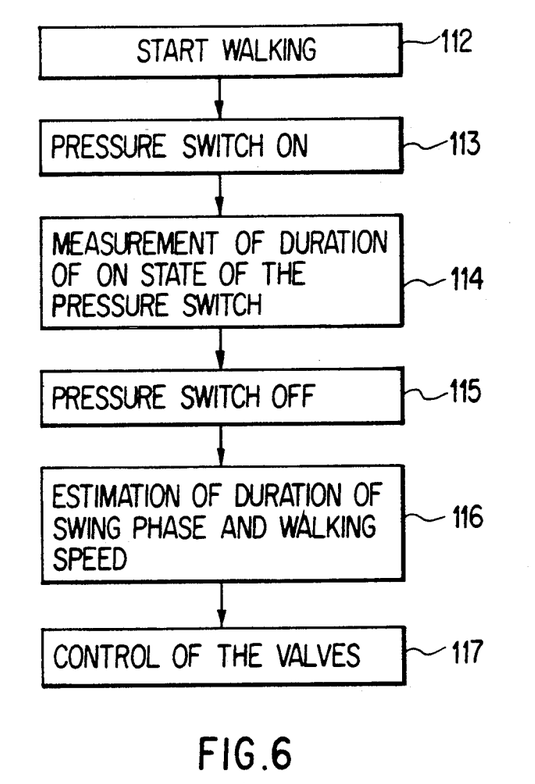
FIG. 6 is a flow chart of assistance in explaining a mode of control operation for controlling the above-knee prosthesis of FIG. 4.

FIG. 6 is a flow chart showing the control sequence provided by the control unit of this embodiment. Walking begins at step 112, the pressure switch is turned on at step 113, the duration of the on state of the pressure switch is measured at step 114, the pressure switch is turned off at step 115, estimation of the duration of the swing phase and walking speed occurs at step 116 and the valve of the air cylinder 105 is controlled at step 117. The knee angle detector 108 may be of any type and may be disposed at any suitable position provided that the knee angle detector 108 is able to detect the angle between the thigh frame 101 and the leg frame 102 when the leg frame 102 is at an angular position in a predetermined angular range from a position where the above-knee prosthesis is extended. For example, the knee angle detector 108 may be a photoelectric switch or a contact limit switch. The control unit comprise a microcomputer and input-output devices, or equivalent hardware logic circuit.

Figure 7:
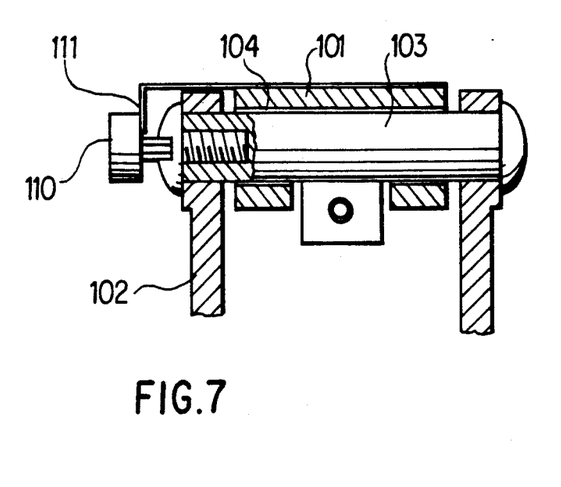
FIG. 7 is a fragmentary longitudinal sectional view showing a modification of the above-knee prosthesis of FIG. 4.

A modification shown in FIG. 7 employs a combination of a potentiometer 110 and a contact member 111 instead of the combination of the proximity detector 108 and the metallic plate 109. The potentiometer 10 is provided on the knee joint pin 103 while the contact member 11 is attached to the thigh frame 101. Since the potentiometer 10 is capable of continuously detecting the variable knee angle, the employment of the potentiometer 10 enables the continuous opening of the valve of the air cylinder 105. However, since only the precise detection of the period of a stance phase, in which the knee angle is within a fixed angular range, is necessary to achieve the object of the present invention, the period of a stance phase is determined by measuring a time period t (FIG. 8(b)) in which the knee angle is below a predetermined threshold angle TH.

Figure 8A:
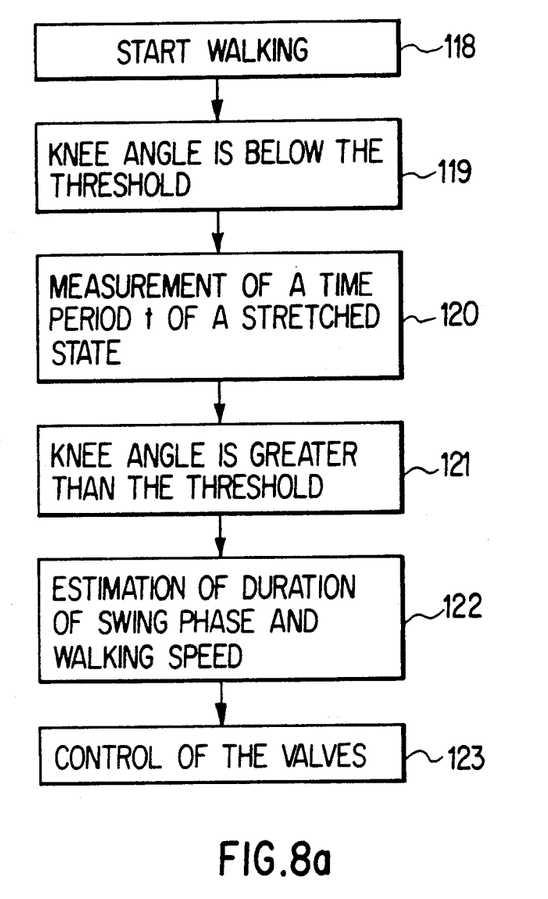
FIGS. 8(a) and 8(b) are a flow chart and a graph, respectively, of assistance in explaining a control operation for controlling the above-knee prosthesis of FIG. 7.

The control of the modification of FIG. 7 operates according to the flow chart of FIG. 8a. Walking begins at step 118, the knee angle being below the threshold TH is detected at step 119, the measurement of a time period t of the knee in an extended state is measured at step 120, the knee angle is determined to be greater than the threshold value *TH in step 121, the duration of the swing phase and the walking speed are estimated at step 122 and the valve of the cylinder 5 is controlled at step 123.

Figure 8B:
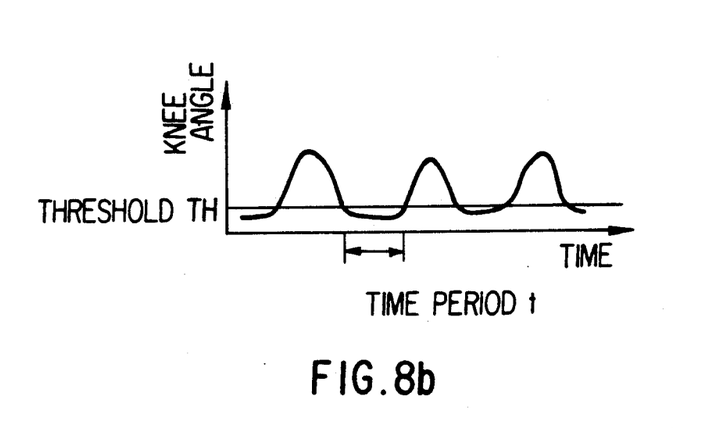

FIG. 8b shows the detection of the value TH, over time. It is below the threshold value TH during the time period t.

Thus, the above-knee prosthesis in the second embodiment is capable of properly controlling the motion of the leg frame according to the variation of the walking speed of the prosthesis wearer between a low walking speed, a middle walking speed and a high walking speed. Furthermore, since the elimination of a pressure switch for detecting load on the leg frame enables constructing the above-knee prosthesis in a lightweight, compact construction, the present invention is effectively applicable to small above-knee prosthesis for women and children. Still further, since the function of the knee angle detector is not affected by the condition of the ground, and the knee angle detector maintains high reliability for an extended period of use, is free from malfunction and facilitates adjustment and maintenance because the knee angle detector does not have any sliding components, the knee angle detector is free from malfunction due to disconnection and readily available in the market, the above-knee prosthesis of the present invention can be manufactured at a reduced cost.

Third Embodiment (FIGS. 9 to 14):

An above-knee prosthesis in a third embodiment according to the present invention includes the air cylinder valve control structure, such as elements 4-12, of the first embodiment, and also incorporates a knee drop-off preventive device.

The above-knee prosthesis in the third embodiment has a thigh frame 201 a leg frame 202 pivotally joined at the upper end thereof to the lower end of the thigh frame 201 by a knee joint pin 203. In this embodiment, the knee joint pin 203 is fixed to the thigh frame 201 so that the leg frame 202 is able to turn thereon. The leg frame 202 is able to turn backward on the knee joint pin 203 from an extended position and is unable to turn forward beyond the extended position. The forward turn of the leg frame 202 beyond the extended position is limited by a rubber pad 204 (FIG. 10) provided on the front side of the upper end of the leg frame 202.

Figure 9:
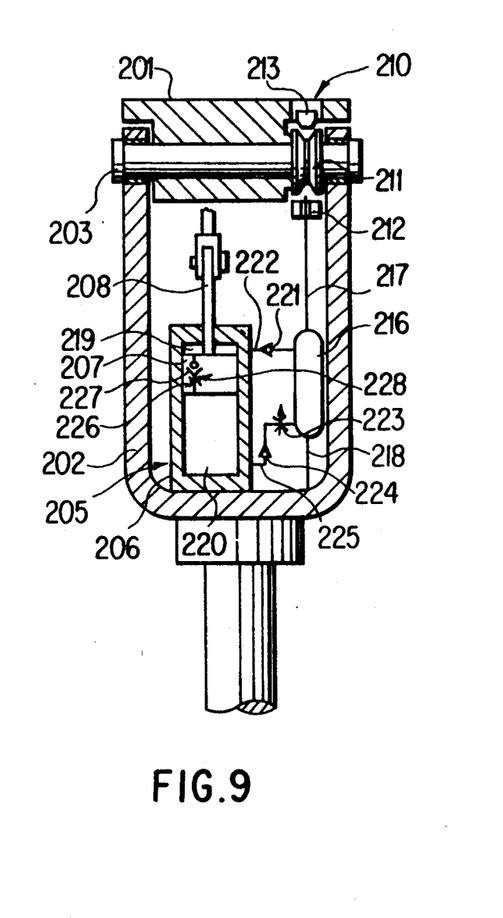
FIG. 9 is a fragmentary longitudinal sectional view of an above-knee prosthesis in a third embodiment according to the present invention.

An air cylinder 205 having a cylinder body 206, a piston 207 and a piston rod 208 is disposed longitudinally in a space within the leg frame 202. The piston rod 208 is linked to the thigh frame 201 via with a link 209. The piston rod 8 may be joined directly to the thigh frame 201.

A braking device 210 is mounted on the knee joint pin 203. The braking device 210 comprises a brake disk 211 fixed to the knee joint pin 203 a lower brake shoe 212 attached to the leg frame 202 so as to be able to engage the lower portion of the brake disk 211 an upper brake shoe 113 pivotally joined to the thigh frame 201 with a pin 214 so as to be able to the upper portion of the brake disk 211, a compression spring 215 provided between the free ends of the lower brake shoe 212 and the upper brake shoe 213 to separate the upper brake shoe 213 from the brake disk 211.

Figures 10, 11, 12A, 12B:
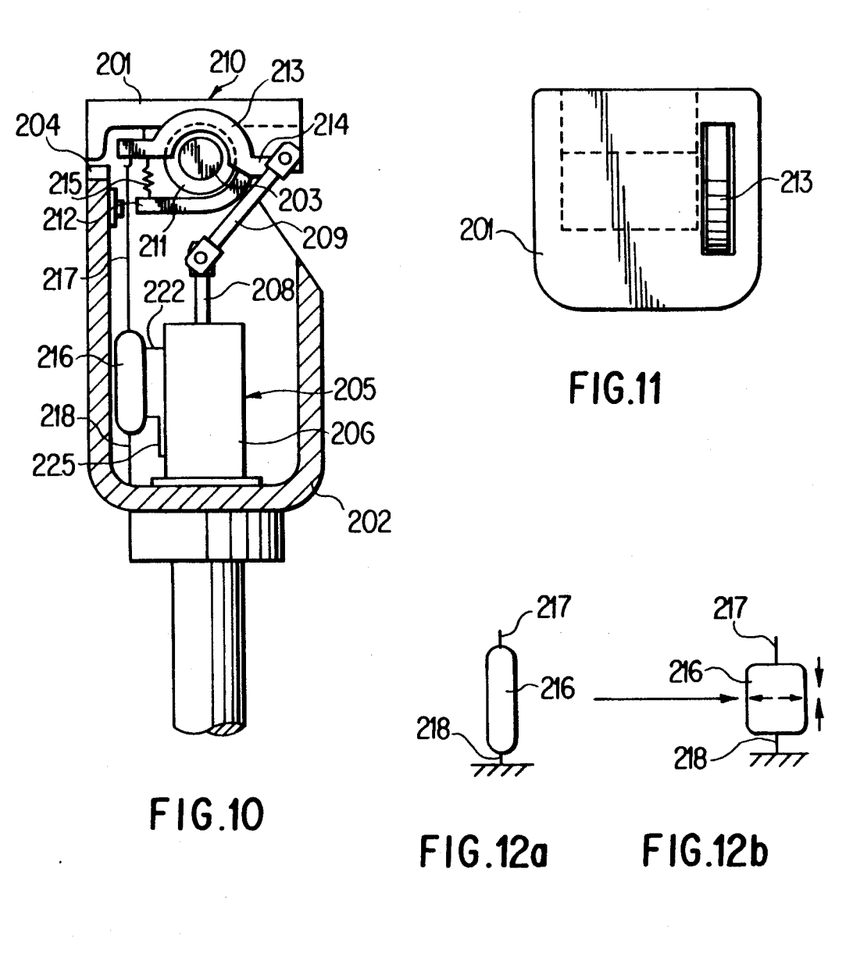
FIG. 10 is a fragmentary side elevation corresponding to FIG. 9.
FIG. 11 is a top plan view of the above-knee prosthesis of FIG. 9.
FIGS. 12(a) and 12(b) are schematic views showing an actuator employed in the above-knee prosthesis of FIG. 9 in a deflated state and in an inflated state, respectively.

An actuator 216 for bringing the upper brake shoe 213 into engagement with the brake disk 211 is provided in a space within the leg frame 202. The actuator 216 has one end connected to the free end of the upper brake shoe 213 by a wire 217 and the other end connected to the leg frame 202 by a wire 218. In this embodiment, the actuator 216 is a rubber tube as shown in FIG. 12(a) which expands laterally and diminishes in length as shown in FIG. 12(b) when air is supplied therein. The actuator 216 may be, for example, a RUBATUATOR ® (Bridgestone Co.) available in the market.

Figure 13:
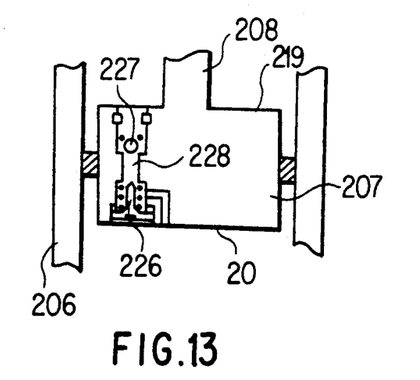
FIG. 13 is a fragmentary longitudinal sectional view of an air cylinder incorporated into the above-knee prosthesis of FIG. 9.

The actuator 216 is connected to the upper chamber 219 of the air cylinder 205 through a line 222 including a check valve 221 and to the lower chamber 20 of the air cylinder 205 through a line 225 including a metering valve 223 and a check valve 224. The check valve 221 allows air to flow only from the upper chamber 219 of the air cylinder 205 into the actuator 216. The check valve 224 allows air to flow only from the actuator 216 into the lower chamber 220 of the air cylinder 205. As best shown in FIG. 13, the upper chamber 219 and the lower-chamber 220 of the air cylinder 205 communicate with each other by means of a passage 228 formed through the piston 207 and provided with a variable metering valve 226 and a check valve 227. The check valve 227 allows air to flow through the passage 228 only from the lower chamber 220 into the upper chamber 219. The passage 228 may be an external passage formed outside the cylinder body 206 so as to interconnect the upper chamber 219 and the lower chamber 220.

When the leg frame 202 swings forward from its rearmost position, the piston 207 moves upward, the check valve 227 is closed and the check valve 221 is opened to allow the air contained in the upper chamber 219 to flow into the actuator 216. Accordingly, the leg frame 202 is able to swing lightly in the initial stage of a forward swing motion. The metering valve 223 restricts the flow rate of air to control the swing speed of the leg frame 202 properly as the leg frame 202 swings forward. As the quantity of air supplied into the actuator 216 increases, the actuator 216 expands laterally and diminishes in length to turn the upper brake shoe 213 gradually on the pin 214 through the wire 217 so that the upper brake shoe 213 engages the brake disk 211 gradually. At the end of the forward swing motion of the leg frame 202 the upper brake shoe 213 engages the brake disk 211 firmly to prevent the drop-off of the above-knee prosthesis after the heel of the above-knee prosthesis has landed on the ground. In the latter stage of a stance phase, the air thus accumulated in the actuator 216 flows gradually through the check valve 224 at a flow rate limited by the metering valve 223 into the lower chamber 220 of the air cylinder 205, so that the pressure within the actuator 216 drops gradually and the actuator 216 is restores its original shape. Consequently, the upper brake shoe 213 is separated from the brake shoe 211 by the resilience of the compression spring 215. A braking period during which the braking device 210 is applied is thus adjusted by the metering valve 223.

During the backward swing motion of the leg frame 202 after the heel of the above-knee prosthesis has departed from the ground, the piston 207 moves downward. Then, the air contained in the cylinder body 206 of the air actuator 205 flows from the lower chamber 220 into the upper chamber 219 through the check valve 227 and the metering valve 226. The flow rate of air flowing from the lower chamber 220 into the upper chamber 219 is limited by the metering valve 226 to limit the speed of swing motion of the leg frame 202 below a predetermined level.

Figure 14:
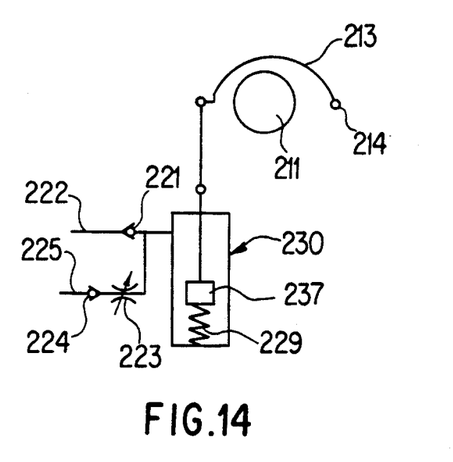
FIG. 14 is a diagrammatic illustration showing a modification of the above-knee prosthesis of FIG. 9.

In a modification shown in FIG. 14, an air cylinder 230 is employed instead of the rubber tube as the actuator 216. The air cylinder 230 is provided with a compression spring 229 in the lower chamber to bias a piston upward. The function of the air cylinder 230 is the same as that of the actuator 216.

The braking device 210 may be of any suitable type.

Thus, in the third embodiment, the swing motion of the leg frame is controlled properly and the leg frame is braked during a stance phase so that the drop-off of the above-knee prosthesis is prevented positively.

Although the present invention has been described in its preferred forms with a certain degree of particularity, obviously many changes and variations are possible therein. It is therefore to be understood that the present invention may be practiced otherwise than specifically described herein without departing from the scope and spirit thereof.

What is claimed is:

1. A method of operating a teaching playback swing-phase-controlled above-knee prosthesis comprising a thigh frame, a leg frame pivotally joined to the thigh frame via at least one knee joint pin, a cylinder interconnecting the thigh and leg frames, said cylinder being provided with an air valve and means for adjusting the opening of the air valve of the cylinder to a plurality of values for a plurality of walking speeds, gait selecting means having a plurality of positions, opening detecting means for detecting a degree of opening of the air valve of the cylinder, opening storage means for storing a plurality of the values of opening of the valve of the cylinder, walking speed determining means for determining an actual walking speed, and control means for adjusting the degree of opening of the air valve of the cylinder to one of said values of opening, said method comprising the steps of:

performing a teaching mode of operation including:
a) setting the gait selecting means to one position,
b) adjusting the opening of the air valve to a value for said one position,
c) detecting and storing the value of the opening of the air valve,
d) permitting a wearer of the prosthesis to walk at a walking speed normal for that wearer with the opening of the air valve having said value,
e) determining and storing said walking speed of the wearer,
f) setting the gait selecting means to at least one other position, and
g) for each said at least one other position, repeating steps (b) through (e), whereby there is stored for each position of said gait selecting means a value of the opening of said air valve and a corresponding walking speed normal for that wearer; and performing a playback mode of operation including:
h) determining the walking speed of the same wearer as in step d),
i) comparing the walking speed determined in step (h) with the walking speeds determined in each performance of the step (e), and
j) adjusting the opening of the air valve to a value based upon the comparison of step (i).

2. The method of claim 1 wherein said walking speed determining means includes phase detecting means for detecting stance phases of walking and wherein said steps (e) and (h) each comprise:

detecting a stance phase period of each step as the wearer walks; and
calculating an average stance period based on the detected stance periods; and
using the average stance phase period to indicate walking speed.

3. The method of claim 2 wherein said positions of said gait selecting means comprise a low speed position, a middle speed position and a high speed position, wherein corresponding values of the air valve opening degree ($S_T$) comprise $S_{SLOW}$, $S_{MID}$ and $S_{FAST}$, respectively, and wherein corresponding average stance phase periods T comprise $T_{SLOW}$, $T_{MID}$ and $T_{FAST}$, respectively.

4. The method of claim 3 wherein:
$S_T = S_{SLOW}$ when $T \geq (T_{SLOW} + T_{MID})/2$,
$S_T = S_{MID}$ when $(T_{MID} + T_{FAST})/2 \leq T \leq (T_{SLOW} + T_{MID})/2$,
$S_T = S_{FAST}$ when $T < (T_{MID} + T_{FAST})/2$.

5. The method of claim 2 including a pressure switch mounted so as to detect a pressure on said leg frame, wherein said stance phase period detecting step comprises measuring a time period during which said pressure switch detects a pressure.

* * * * *

UNITED STATES PATENT AND TRADEMARK OFFICE
CERTIFICATE OF CORRECTION

PATENT NO. : 5,133,774
DATED : JULY 28, 1992
INVENTOR(S) : SEISHI SAWAMURA ET AL

It is certified that error appears in the above-identified patent and that said Letters Patent is hereby corrected as shown below:

On the title page, item [73] under the heading of "Assignee" after "Kobe, Japan", please insert --Hyogo-ken Shakaifukushijigyodan, Kobe, Japan--.

Signed and Sealed this

Seventeenth Day of May, 1994

*Attest:*

BRUCE LEHMAN

*Attesting Officer*     *Commissioner of Patents and Trademarks*